(12) United States Patent
Makimura et al.

(10) Patent No.: US 11,560,602 B2
(45) Date of Patent: Jan. 24, 2023

(54) PRIMER SET FOR DETECTING TRICHOPHYTON GENE BY LAMP METHOD, KIT INCLUDING SAME, AND METHOD FOR DETECTING TRICHOPHYTON USING SAME

(71) Applicants: SATO PHARMACEUTICAL CO., LTD., Tokyo (JP); TEIKYO UNIVERSITY, Tokyo (JP)

(72) Inventors: Koichi Makimura, Tokyo (JP); Kazuo Satoh, Tokyo (JP); Yoshiharu Miyajima, Tokyo (JP)

(73) Assignees: SATO PHARMACEUTICAL CO., LTD., Tokyo (JP); TEIKYO UNIVERSITY, Tokyo (JP)

( * ) Notice: Subject to any disclaimer, the term of this patent is extended or adjusted under 35 U.S.C. 154(b) by 0 days.

(21) Appl. No.: 16/971,513

(22) PCT Filed: Feb. 15, 2019

(86) PCT No.: PCT/JP2019/005614
§ 371 (c)(1),
(2) Date: Aug. 20, 2020

(87) PCT Pub. No.: WO2019/163672
PCT Pub. Date: Aug. 29, 2019

(65) Prior Publication Data
US 2020/0385820 A1 Dec. 10, 2020

(30) Foreign Application Priority Data
Feb. 22, 2018 (JP) .............................. JP2018-029718

(51) Int. Cl.
*C12Q 1/68* (2018.01)
*C12Q 1/6895* (2018.01)
*C12Q 1/6853* (2018.01)

(52) U.S. Cl.
CPC ......... *C12Q 1/6895* (2013.01); *C12Q 1/6853* (2013.01)

(58) Field of Classification Search
None
See application file for complete search history.

(56) References Cited

U.S. PATENT DOCUMENTS

| | | | |
|---|---|---|---|
| 6,410,278 | B1 | 6/2002 | Notomi et al. |
| 7,175,985 | B1 | 2/2007 | Kanda et al. |
| 2002/0168676 | A1 | 11/2002 | Notomi et al. |
| 2004/0038253 | A1 | 2/2004 | Nagamine |
| 2004/0132144 | A1 | 7/2004 | Notomi et al. |
| 2007/0238113 | A1 | 10/2007 | Kanda et al. |
| 2008/0213790 | A1 | 9/2008 | Nagamine |
| 2008/0213842 | A1 | 9/2008 | Nagamine |
| 2009/0098566 | A1 | 4/2009 | Notomi et al. |
| 2010/0311041 | A1* | 12/2010 | Brillowska-Dabrowska ............... C12Q 1/6895 435/6.12 |
| 2012/0309005 | A1 | 12/2012 | Makimura et al. |
| 2017/0029906 | A1 | 2/2017 | Divakar et al. |
| 2017/0107568 | A1 | 4/2017 | Notomi et al. |

FOREIGN PATENT DOCUMENTS

| | | |
|---|---|---|
| CN | 104087679 A | 10/2014 |
| JP | 2001242169 A | 9/2001 |
| JP | 2007124970 A | 5/2007 |
| JP | 2007228868 A | 9/2007 |
| JP | 2008067605 A | 3/2008 |
| WO | 0028082 A1 | 5/2000 |
| WO | 0224902 A1 | 3/2002 |
| WO | 2011068218 A1 | 6/2011 |
| WO | 2014/133153 A1 | 9/2014 |
| WO | WO-2016011280 A1 * | 1/2016 ............. B01L 7/525 |

OTHER PUBLICATIONS

Lowe et al. A computer program for selecting oligonucleotide primers for polymerase chain reaction. Nucleic Acids Research, vol. 18(7), p. 1751-1761,(1990).*
M. Ebihara et al.; "Molecular detection of dermatophytes and nondermatophytes in onychomycosis by nested polymerase chain reaction based on 28S ribosomal RNA gene sequences"; BJD British Journal of Dermatology; 2009 pp. 1038-1044; vol. 161; No. 5.
International Search Report issued in PCT/JP2019/005614; dated May 14, 2019.
Ayaka Yo et al.; "Detection and identification of Trichophyton tonsurans from clinical isolates and hairbrush samples by loop-mediated isothermal amplification system"; Journal of Dermatology; vol. 43, No. 9; Feb. 19, 2016; pp. 1037-1043; XP055633740; DOI: 10.1111/1346-8138.13303.
The extended European search report issued by the European Patent Office dated Oct. 13, 2021, which corresponds to European Patent Application No. 19756930.4-1118 and is related to U.S. Appl. No. 16/971,513.
Hiroshi Takano et al.; "Loop-mediated isothermal amplification (LAMP); Principle and applications"; Modem Media; 2014; pp. 211-231; vol. 60.
International Preliminary Report on Patentability and Written Opinion issued in PCT/JP2019/005614; dated Aug. 27, 2020.

* cited by examiner

*Primary Examiner* — Suryaprabha Chunduru
(74) *Attorney, Agent, or Firm* — Studebaker & Brackett PC (57) ABSTRACT

The present invention has an object to provide a simpler and quicker method for diagnosing tinea, method for detecting a *Trichophyton*, or method for detecting the *Trichophyton* gene. Use of at least four kinds of specific primers each designed based on a DNA sequence of the *Trichophyton* gene makes it possible to simply and quickly detect the *Trichophyton* gene.

9 Claims, 1 Drawing Sheet
Specification includes a Sequence Listing.

PRIMER SET FOR DETECTING TRICHOPHYTON GENE BY LAMP METHOD, KIT INCLUDING SAME, AND METHOD FOR DETECTING TRICHOPHYTON USING SAME

REFERENCE TO AN ELECTRONIC SEQUENCE LISTING

The contents of the electronic sequence listing (sequence-listing.txt; Date of Creation: Aug. 19, 2020; and Size: 7,915 bytes) is herein incorporated by reference in its entirety.

TECHNICAL FIELD

The present invention relates to a primer set for detecting a *Trichophyton* gene by a LAMP method, a kit containing the primer set, and a method for detecting the gene by using them.

BACKGROUND ART

Tinea is a type of fungal disease that causes an infection at skin keratin or nails. Dermatophytes such as *Trichophyton rubrum* (*T. rubrum*) and *Trichophyton mentagrophytes* (*T. mentagrophytes*) account for 90% or more of tinea-causative fungi detected in tinea patients. Other tinea-causative fungi are a *Candida* fungus (particularly, *Candida albicans*), an *Aspergillus* fungus, a *Fusarium* fungus, and the like.

The prevalence of tinea pedis and tinea unguium patients in Japan is said to be 25% for tinea pedis and 10% for tinea unguium. On the other hand, there are many non-infectious diseases with findings resembling tinea symptoms. A result obtained from patients each receiving a check-up with tinea as a chief complaint is that about ⅔ of the patients actually had tinea and the other patients did not have tinea. For this reason, there is a need for a simpler and quicker method for diagnosing tinea in order to select an appropriate treatment method.

As a method for diagnosing tinea, a method is known in which a specimen (a nail, keratin, or the like) collected from an affected area is analyzed by a direct microscopic method or a culture method. The direct microscopic method is a method of fusing protein with potassium hydroxide to expose fungus bodies, and then observing the fungus bodies with a microscope. The culture method is a method of culturing fungi on a selective medium for several weeks and observing colonies and the like in detail to identify the fungal species.

In recent years, with the advancement of molecular biology, it has become possible to use a nucleic acid amplification detection method for fungus-derived nucleic acids in order to identify a tinea-causative fungus, and methods using real-time PCR and nested PCR have been reported (Patent Literature 1 and Non-Patent Literature 1).

On the other hand, the LAMP method is a method of amplifying DNA quickly at a fixed temperature, and is a method that allows the amplified DNA to be confirmed even by a visual check through measurement such as turbidity or fluorescence detection (Patent Literatures 2 to 4). As previous reports using this method, methods for detecting *Bordetella pertussis*, diphtheria toxin, and so on have been known (Patent Literatures 5 and 6), but a method for detecting a *Trichophyton* using the LAMP method is not known.

CITATION LIST

Patent Literatures

Patent Literature 1: Japanese Patent Application Publication No. 2008-067605
Patent Literature 2: International Publication No. WO00/28082
Patent Literature 3: International Publication No. WO02/24902
Patent Literature 4: Japanese Patent Application Publication No. 2001-242169
Patent Literature 5: Japanese Patent Application Publication No. 2007-124970
Patent Literature 6: Japanese Patent Application Publication No. 2007-228868

Non Patent Literatures

Non Patent Literature 1: M. Ebihara et al., Br J Dermatol. 161 (5): 1038-44; 2009

SUMMARY OF INVENTION

Problems to be Solved by the Invention

The direct microscopic method has difficulty in identifying a fungi species, entails high false positives, and requires skilled techniques even to confirm the presence of fungal elements. The fungal culture method requires several weeks to obtain a result and also has low sensitivity. In particular, it is difficult to culture specimens derived from tinea unguium, so that skilled techniques are required to collect specimens. Meanwhile, the nested PCR method and real-time PCR method require a thermal cycler for stringent temperature control, and indispensably require an electrophoresis device or a real-time fluorescence measuring device to confirm the amplified DNA. Since these methods require precise operations in laboratories, they have not been used as diagnostic methods in clinical settings.

Therefore, the present invention has an object to provide a simpler and quicker method for diagnosing tinea, method for detecting a *Trichophyton*, or method for detecting the *Trichophyton* gene.

Means for Solution of the Problems

As a result of earnest studies to achieve the above object, the present inventors have found that use of at least four kinds of specific primers designed based on a DNA sequence of the *Trichophyton* gene enables simple and quick detection of the *Trichophyton* gene by a LAMP method, and thereby completed the present invention.

In sum, the present invention provides a primer set, a kit containing the primer set, and a method using them, which will be described below.

<1> A primer set for detecting the *Trichophyton* gene by a LAMP method, comprising four kinds of oligonucleotides containing base sequences represented by SEQ ID NOs: 1 to 4 or four kinds of oligonucleotides containing base sequences represented by SEQ ID NOs: 7 to 10.

<2> The primer set according to the above <1>, further comprising at least one kind of loop primer.

<3> The primer set according to the above <2>, wherein the loop primer is an oligonucleotide containing a complementary base sequence in a range of at least one base sequence selected from base sequences represented by SEQ ID NOs: 13 to 16.

<4> The primer set according to the above <2> or <3>, wherein the loop primer is an oligonucleotide containing a base sequence selected from the group consisting of base sequences represented by SEQ ID NOs: 5, 6, 11, and 12.

<5> The primer set according to any one of the above <1> to <4>, wherein the *Trichophyton* is *T. rubrum* or *T. mentagrophytes*.

<6> A kit for detecting a *Trichophyton* in a sample, comprising the primer set according to any one of the above <1> to <5>.

<7> The kit according to the above <6>, wherein the *Trichophyton* is *T. rubrum* or *T. mentagrophytes*.

<8> A method for detecting a *Trichophyton* in a sample, comprising the steps of:

amplifying a nucleic acid in the gene by a LAMP method using the primer set according to any one of the above <1> to <5> or the kit according to the above <6> or <7>; and detecting the amplified nucleic acid.

<9> The method according to the above <8>, wherein the amplified nucleic acid is detected by turbidity measurement, fluorescence measurement using a fluorescent substance, immunochromatography, nucleic acid hybridization, or electrophoresis.

<10> The method according to the above <8> or <9>, wherein the *Trichophyton* is *T. rubrum* or *T. mentagrophytes*.

Advantageous Effects of Invention

According to the present invention, it is possible to simply and quickly detect the gene of a *Trichophyton* by the LAMP method. Then, the present invention produces the following advantageous effect on the diagnosis of tinea or the detection of a *Trichophyton*.

1. For example, in the case of identifying a *Trichophyton* from a nail or skin keratin specimen, it is possible to achieve highly sensitive detection in a short period of time, like a case where the presence of *T. rubrum* or *T. mentagrophytes* can be examined in about two days including a DNA extraction step.

2. The nucleic acid amplification by the LAMP method makes it possible to determine the presence or absence of an amplification product by various methods such as turbidity measurement, fluorescence measurement using a fluorescent substance, immunochromatography, nucleic acid hybridization, and electrophoresis, and in particular, the measurement of detected turbidity or the fluorescence measurement using a fluorescent substance are capable of making the determination within a shorter period of time than the other methods.

3. Since there is no need for skilled technique, the presence of a *Trichophyton* can be determined mechanically.

4. There is no need for time and effort for selecting and preparing a selective medium appropriate for determining a target fungus.

DESCRIPTION OF EMBODIMENTS

A "*Trichophyton*" described in the present specification refers to a fungus in a genus such as *Trichophyton*, *Microsporum*, or *Epidermophyton* genera. The dermatophyte may be, for example, *T. rubrum*, *T. mentagrophytes*, *T. tonsurans*, or *Microsporum canis*, and may be preferably *T. rubrum* or *T. mentagrophytes*.

The "*Trichophyton* gene" described in the present specification refers to a gene characteristic of the genus or species of the *Trichophyton*, and can be useful for identifying the genus or species. The *Trichophyton* gene may be, for example, the gene of *T. rubrum*, *T. mentagrophytes* or *T. tonsurans*, and may be preferably the gene of *T. rubrum* with GenBank Accession No. U18352 (SEQ ID NO: 13) or the gene of *T. mentagrophytes* with GenBank Accession No. KC146353 (SEQ ID NO: 14) as shown in Table 1.

TABLE 1

Examples of Trichophyton Genes

| GenBank Accession No. | Base Sequence | | | | | |
|---|---|---|---|---|---|---|
| U18352 (SEQ ID NO: 13) | aagtaaaagt ggcccccccac ttgtctacct ttctgggagc tcagtctgag tgaagaacgc cacattgcgc tgtgtgatgg cgattccggc tttatatata caataagcgg | cgtaacaagg gatagggacc cacccggttg ctcgagccgg cgtttagcaa agcgaaatgc cctctggcat acgaccgtcc ttcctaggcg tatatatctt | tttccgtagg gacgttccat cctcggcggg accgcgcccg gcacaatcag gataagtaat tccgggggggc ggcccctccc aatgggcagc ttcaggttga | tgaacctgcg caggggtgag ccgcgctccc ccggaggaca ttaaaacttt gtgaattgca atgcctgttc ttcggggggcg caattcagcg cctcggatca | gaaggatcat cagacgtgcg cctgccaggg gacaccaaga caacaacgga gaattccgtg gagcgtcatt ggacgcgccc ccctcaggac ggtagggata | taacgcgcag ccggccgtac agagccgtcc aaaaattctc tctcttggtt aatcatcgaa tcaaccccctc gaaaagcagt cggccgccct cccgctgaac | gccggaggct gcccccattc ggcgggcccc tgaagagctg ccggcatcga tctttgaacg aagcccggct ggccaggccg ggccccaatc ttaagcatat |
| KC146353 (SEQ ID NO: 14) | ggtttccgta caaacgtccg gcctcggcgg gcgcccgccg aatcagttaa agtaatgtga gggggcatgc cccccgtctt aatgggcaac tgacctcgga | ggtgaacctg tcaggggtga gccgcgctct gaggacagac aactttcaac attgcagaat ctgttcgagc tgggggtgcg aaaccagcgc tcaggtaggg | cggaaggatc gcagatgtgc cccaggagag gcaaaaaaat aacggatctc tccgtgaatc gtcatttcag ggacgcgccc ctccaggacc atacccgctg | attagcgcgc gccggccgta ccgttcggcg tctttcagaa ttggttccgg atcgaatctt ccctcaagc gaaaagcagt ggccgccctg aacttaagca | aggccggagg ccgccccatt agcctctctt gagctgtcag catcgatgaa tgaacgcaca cggcttgtg ggccaggccg gcctcaaaat t | ctggcccccc cttgtctaca tagtggctaa tctgagcgtt gaacgcagcg ttcgccccc tgatgacga cgattccggc ctgttttata | acgatagggc ttactcggtt acgctggacc agcaagcaaa aaatgcgata tggcattccg ccgtccggcg ttcctaggcg cttatcaggt |

The "LAMP method" described in the present specification refers to a gene amplification method using multiple primers, which produces an amplification product with hairpin structures at ends by a strand displacement reaction that proceeds continuously under isothermal conditions as described in Patent Literatures 2 to 4 listed above. First, in the initial reaction, two inner primers (FIP and BIP), two outer primers (F3 primer and B3 primer) and a strand displacement-type DNA polymerase are used to synthesize, from a template DNA, a dumbbell-shaped structure with single-stranded loops at both ends. This structure serves as the initiating structure of the amplification cycle, and the DNA elongation/synthesis reaction proceeds from the 3'-end side of this structure using itself as a template. The amplification product is composed of a large number of repeating structures, and the unit of the repeating structure includes complementary regions in the same strand in which two base sequences of nucleic acids constituting the amplified regions between the primers are reverse to each other. When the template is RNA, the initiating structure can be similarly synthesized by adding a reverse transcriptase to a reaction solution composition for a DNA template, and then the amplification can be allowed to proceed (Patent Literature 2).

As described above, the LAMP method requires at least four kinds of primers. In a target DNA to be amplified, regions F3c, F2c, and F1c are defined in order from the 3'-end side, and regions B3, B2, and B1 are defined in order from the 5'-end side. Then, the at least four kinds of primers are designed based on base sequences of oligonucleotides substantially identical or complementary to at least these six regions. The terms, identical or complementary, used to characterize the base sequences constituting the oligonucleotides do not have to be completely identical or completely complementary. That is, the term "identical" to a certain sequence can also include a sequence complementary to a base sequence capable of hybridizing to the certain sequence. On the other hand, the term "complementary" means a sequence that is capable of hybridizing under stringent conditions and providing the 3' end to serve as an initiator of complementary strand synthesis. The "stringent conditions" refer to salt concentration and/or temperature conditions in which only specific hybridization occurs and non-specific hybridization does not occur, and may be conditions where, for example, an amplification reaction solution containing KCl, MgSO$_4$ and/or (NH$_4$)$_2$SO$_4$ in amounts of 5 to 15 mM is incubated at 55 to 70° C.

Each of the primers designed based on the base sequences of the target DNA constitutes one of FIP, F3 primer, BIP, and B3 primer. The FIP is designed such that the 3' end has a base sequence of an F2 region substantially complementary to the F2c region of the target DNA and the 5' end has a base sequence substantially identical to that of the F1c region of the target DNA. In this case, a sequence independent of the target DNA may be interposed between the F2 and F1c sequences. The sequence length of the sequence independent of the target DNA may be 0 to 50 bases and preferably 0 to 40 bases. The F3 primer is designed to have a base sequence that is substantially identical to that of an F3 region substantially complementary to the F3c region of the target DNA. The BIP is designed such that the 3' end has a base sequence of the B2 region substantially complementary to a B2c region of the target DNA and the 5' end has a base sequence substantially identical to that of a B1c region of the target DNA. Also in the BIP, a sequence independent of the target DNA may be interposed between the B2 and B1c sequences as in the FIP. The B3 primer is designed to have a base sequence that is substantially identical to that of the B3 region substantially complementary to a B3c region of the target DNA.

The "four kinds of oligonucleotides" contained in the primer set of the present invention are equivalent to the FIP, the F3 primer, the BIP, and the B3 primer, and can be designed based on the base sequence of the *Trichophyton* gene. The length of the FIP or BIP may be 30 to 50 bases and preferably 35 to 45 bases. The length of the F3 primer or B3 primer may be 15 to 25 bases and preferably 18 to 22 bases. Table 2 presents examples of the F3c, F2c, F1c, B1, B2, and B3 regions in the base sequences of the *Trichophyton* genes.

TABLE 2

F3c, F2c, F1c, B1, B2, and B3 regions of *Trichophyton* Genes

| Region | GenBank Accession No. U18352 (*T. rubrum*) | GenBank Accession No. KC146353 (*T. mentagrophytes*) |
| --- | --- | --- |
| F3c | 43 to 61 positions | 19 to 37 positions |
| F2c | 82 to 99 positions | 57 to 75 positions |
| F1c | 122 to 141 positions | 106 to 124 positions |
| B1 | 144 to 165 positions | 127 to 148 positions |
| B2 | 209 to 225 positions | 183 to 204 positions |
| B3 | 242 to 260 positions | 219 to 236 positions |

Table 3 presents an example of loop primers and their base sequences in the present invention, but primers substantially identical to them may be also used. To be more specific, the base sequence of each primer may have a loss, substitution, and/or addition of one to several bases as long as the primer has a function to amplify the target gene by the LAMP method.

TABLE 3

Primers Used to Detect Trichophyton Gene

| Primer | Base Sequence | SEQ ID NO |
| --- | --- | --- |
| <For Detection of Gene of T. rubrum> | | |
| TrF3 | AGGATCATTAACGCGCAGG | 1 |
| TrB3 | TCTTGGTGTCTGTCCTCCG | 2 |
| TrFIP | AGAATGGGGCGTACGGCCGATAGGGACCGACGTTCCA | 3 |
| TrBIP | TCTACCTCACCCGGTTGCCTCGTCGAGGCTCCCAGAAGG | 4 |
| <For Detection of Gene of T. mentagrophytes> | | |
| TmF3 | TGCGGAAGGATCATTAGCG | 7 |
| TmB3 | TTTTGCGTCTGTCCTCCG | 8 |
| TmFIP | CAAGAATGGGGCGGTACGGCCCCACGATAGGGCCAAAC | 9 |
| TmBIP | TACATTACTCGGTTGCCTCGGCGCGTTTAGCCACTAAAGAGAGG | 10 |

The "loop primer" described in the present specification refers to a primer containing a sequence complementary to a single-stranded part of the loop at the 5'-end side of the dumbbell-shaped structure (for example, between the B1 and B2 regions or between the F1 and F2 regions). In the LAMP method, the initiators of DNA synthesis can be increased by using at least one of the above loop primers in combination, so that the amplification time can be shortened (Patent Literature 3). The loop primer is designed to hybridize to a loop region to which the FIP or BIP formed in the DNA synthesis process does not hybridize.

In an embodiment, the primer set may contain at least one kind of loop primer. The optional loop primer may be designed within a range of 100 to 121 positions or 166 to 208 positions in U18352 or 76 to 105 positions or 149 to 182 positions in KC146353. The length of the loop primer may be 10 to 25 bases or preferably 15 to 20 bases.

Table 4 presents an example of loop primers and their base sequences in the present invention, but primers substantially identical to them may be also used. To be more specific, the base sequence of each primer may have a loss, substitution, and/or addition of one to several bases as long as the primer has a function to amplify the target gene by the LAMP method.

TABLE 4

Loop Primer

| Primer | Base Sequence | SEQ ID NO |
|---|---|---|
| <For Detection of Gene of T. rubrum> | | |
| TrLF | ACGTCTGCTCACCCCTGA | 5 |
| TrLB | CCGCGCTCCCCCTGC | 6 |
| <For Detection of Gene of T. mentagrophytes> | | |
| TmLF | TCTGCTCACCCCTGACGGAC | 11 |
| TmLB | TCTCCCAGGAGAGCCGT | 12 |

In an embodiment, the primer set of the present invention is included in a "kit for detecting a *Trichophyton* in a sample". The kit may include, for example, a Bst DNA polymerase, a reaction buffer, dNTPs, a positive control DNA, a reaction tube, or an instruction manual in addition to the primer set.

The "sample" described in the present specification refers to a *Trichophyton*, its gene, or a composition containing any of them. As the sample, various kinds of samples can be employed, and examples thereof include specimens of tinea patients or patients suspected of having tinea, or strains cultured in a laboratory. The specimen may be the skin or a skin appendage such as a nail or hair, which may be directly collected from a living body, or be one adhered to clothes or daily necessities or dispersed in the environment. A nucleic acid such as DNA or RNA can be extracted from the sample by a well-known method and used as a template for the LAMP method.

The step of "amplifying a nucleic acid by a LAMP method" described in the present specification may use any of the LAMP methods used in this technical field without limitation, such as the method described in the package insert of a DNA amplification reagent kit (Eiken Chemical Co., Ltd., product No. LMP206). For example, a primer mixture liquid containing the primer set, a Bst DNA polymerase, dNTPs, and distilled water are mixed, and the resultant mixture is dispensed into a reaction tube, to which then the sample or the nucleic acid extracted from the sample is added as a template. The reaction tube is subjected to incubation, for example, for 30 to 90 minutes at 55 to 70° C. and preferably 60 to 65° C. to amplify the nucleic acid. The primer mixture liquid may be prepared by mixing the FIP, the F3 primer, the BIP, and the B3 primer at a molar ratio of 6 to 10:0.5 to 1.5:6 to 10:0.5 to 1.5 and preferably a ratio of 7 to 9:0.8 to 1.2:7 to 9:0.8 to 1.2. In the case of using the optional loop primers LF and LB, the primer mixture liquid may be prepared by mixing the FIP, the F3 primer, the BIP, the B3 primer, and the loop primers LF and LB at a molar ratio of 6 to 10:0.5 to 1.5:6 to 10:0.5 to 1.5:2 to 6:2 to 6 and preferably a ratio of 7 to 9:0.8 to 1.2:7 to 9:0.8 to 1.2:3 to 5:3 to 5.

The "step of detecting the amplified nucleic acid" described in the present specification may be executed by any known method. For example, the amplified nucleic acid may be detected by turbidity measurement, fluorescence measurement using a fluorescent substance, immunochromatography, nucleic acid hybridization, or electrophoresis on the liquid containing the amplification product, and the detection can be performed by a visual check. In the case of turbidity measurement, the turbidity may be measured over time by a real-time turbidity measuring device, or the turbidity of the final product may be measured by a turbidity measuring device. In the case of fluorescence measurement, for example, a fluorescent substance is added to the reaction tube, and the fluorescence may be measured by a real-time PCR device, or the fluorescence of the final product may be measured by a fluorometer. As the fluorescent substance, various kinds of substances used for analysis of nucleic acids in solutions or analysis of the progress degree of the LAMP reaction. For example, the fluorescent substance may be an intercalator such as YO-PRO-1 or SYBR Green or calcein that is activated by a by-product (such as pyrophosphate ion) of the LAMP reaction.

In the case where the sample contains the target gene, the gene is amplified in the amplifying step. On the other hand, in the case where the sample does not contain the target gene, no nucleic acid is amplified. Therefore, according to the present invention, it is possible to detect whether the sample contains a *Trichophyton*, and thereby detect the *Trichophyton* or make diagnoses of tinea patients. In addition, the primer sets target the genes derived from different *Trichophyton* species, and are therefore capable of diagnosing whether a patient is infected with any one or both of *T. rubrum* and *T. mentagrophytes*.

Hereinafter, the present invention will be described specifically by using Examples, but the scope of the present invention should not be limited to these Examples.

EXAMPLES

Example 1

This Example demonstrates that the four kinds of oligonucleotides of the present invention are capable of functioning as a primer set in the LAMP method and amplifying the target gene.

A plasmid DNA was extracted from *T. rubrum* genetically modified *E. coli* by using QIAGEN Plasmid Midi Kit (QIAGEN K.K., product No. 12143). As a 2×DNA amplification reagent and a Bst DNA polymerase for the LAMP method, those commercially available as the DNA amplification reagent kit (Eiken Chemical Co., Ltd., product No. LMP206) were used. A LAMP amplification reaction solution was prepared by mixing 12.5 µL of the 2×DNA amplification reagent, 2.6 µL of a 100 µM primer mixture liquid (TrF3:TrB3:TrFIP:TrBIP=1:1:8:8 (molar ratio)), 2.5 µL of 10 µM YO-PRO-1 (Invitrogen, product No. Y3603), 1.0 µL of the Bst DNA polymerase, 2.0 µL of the plasmid DNA ($1.4 \times 10^{10}$ copies), and at most 25 µL of UltraPure™ DNase/RNase-Free Distilled Water (Invitrogen, product No. 10977). As a negative control, a LAMP amplification reaction solution not containing the plasmid DNA was prepared.

The LAMP amplification reaction solutions were incubated at 57° C., and the fluorescence was measured in 2-min cycles.

Figure 1:
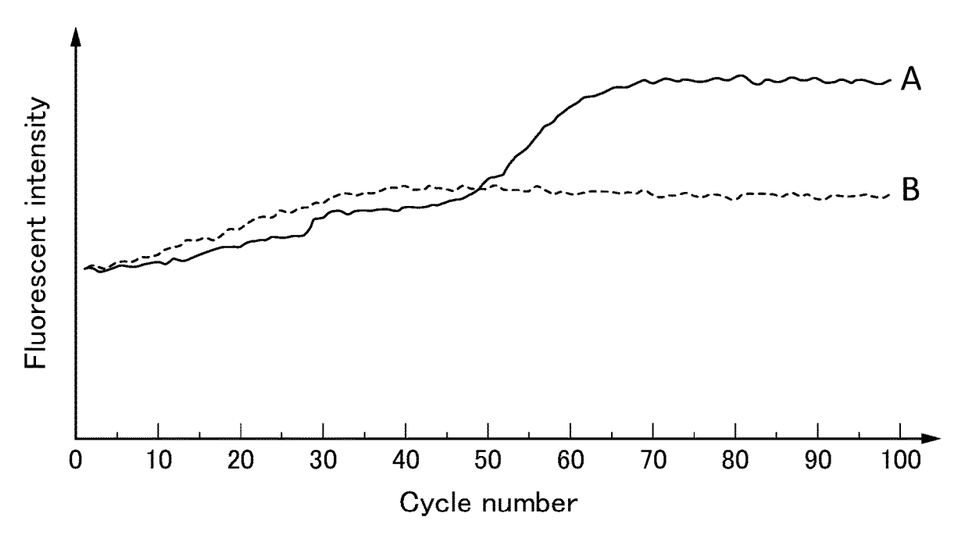
FIG. 1 presents a fluorescence measurement result of DNA amplified by a LAMP method using a primer set containing four kinds of oligonucleotides in the present invention.

The results are presented in FIG. 1. The LAMP amplification solution (A) containing the plasmid DNA containing the target gene of *T. rubrum* demonstrates an increase in the fluorescent intensity from 50 cycles, while the negative control (B) demonstrates no increase in the fluorescent intensity. This indicates that the four kinds of primers TrF3, TrB3, TrFIP, and TrBIP amplified the target gene of *T. rubrum*. Therefore, it is found that the primer set containing the four kinds of oligonucleotides of the present invention is useful to detect the *Trichophyton* gene by the LAMP method.

Example 2

This Example demonstrates that the four kinds of oligonucleotides and the two kinds of loop primers of the present invention are capable of functioning as a primer set in the LAMP method and amplifying the target gene.

As a template DNA, a plasmid DNA or a genomic DNA was used. The plasmid DNA was extracted from *T. rubrum* genetically modified *E. coli* or *T. mentagrophytes* genetically modified *E. coli* by using QIAGEN Plasmid Midi Kit. The genomic DNA was extracted, by using QIAamp® DNA Micro Kit (QIAGEN K. K., product No. 56304), from a nail specimen found to be infected with *T. rubrum* or *T. mentagrophytes* by known means. The primer mixture liquid was prepared by mixing a primer set for *T. rubrum* detection (TrF3, TrB3, TrFIP, TrBIP, TrLF, and TrLB; a primer set Tr) or a primer set for *T. mentagrophytes* detection (TmF3, TmB3, TmFIP, TmBIP, TmLF, and TmLB; a primer set Tm) at a ratio of F3:B3:FIP:BIP:LF:LB=1:1:8:8:4:4. As presented in Table 5, the LAMP amplification reaction solution was prepared, and an amplification reaction was allowed to proceed. The signal of the fluorescent substance (YO-PRO-1) that was intercalated into the amplified DNA was measured by a real-time PCR device (Applied Biosystems Japan Ltd., Step One Plus, CT-97).

TABLE 5

Composition of LAMP Amplification Reaction Solution and Amplification Reaction Conditions

|  | For *T. rubrum* Detection | For *T. mentagrophytes* Detection |
|---|---|---|
| 1. Reaction Solution |  |  |
| 2× DNA Amplification Reagent | 12.5 μL | 12.5 μL |
| Primer Mixture Liquid (100 μM) | 2.6 μL (Primer Set Tr) | 1.3 μL (Primer Set Tm) |
| YO-PRO-1 (10 μM) | 2.5 μL | 2.5 μL |
| Bst DNA Polymerase | 1.0 μL | 1.0 μL |
| Template DNA | 2.0 μL | 2.0 μL |
| UltraPure ™ DNase/RNase-Free Distilled Water | Up to 25 μL | Up to 25 μL |
| 2. Amplification Reaction |  |  |
| Amplification Conditions | 65° C., 1 min (110 Cycles) | 63° C., 1 min (110 Cycles) |
| Stop Conditions | 95° C., 2 min | 95° C., 2 min |

Table 6 presents a cycle number (Ct value) at which the fluorescent intensity exceeds a threshold. In the reaction solution using the primer set Tr, the template DNA containing the gene of *T. rubrum* was amplified. In the reaction solution using the primer set Tm, the template DNA containing the gene of *T. mentagrophytes* was amplified. Therefore, it is found that the target gene of *T. rubrum* or *T. mentagrophytes* can be amplified and detected by the primer set Tr or the primer set Tm, respectively.

TABLE 6

Amplified Template DNA and Ct Value

| Fungus Species | Template DNA | Ct Value |
|---|---|---|
| <Reaction Solution for *T. rubrum* Detection> | | |
| *T. rubrum* | Plasmid ($10^4$ copies/well) | 28 |
| *T. rubrum* | Genomic DNA (10 ng/well) | 28 |
| <Reaction Solution for *T. mentagrophytes* Detection> | | |
| *T. mentagrophytes* | Plasmid ($10^4$ copies/well) | 18 |
| *T. mentagrophytes* | Genomic DNA (10 ng/well) | 30 |

Example 3

This Example demonstrates a specificity of a reaction using each primer set.

Using, as template DNAs, appropriate amounts (5 to 100 ng) of *Trichophyton*-negative nail-derived DNA and genomic DNA derived from each of 16 fungal species, DNA amplification and detection using a reaction solution containing the primer set Tr or the primer set Tm were performed according to the method described in Example 2. Table 7 presents a reaction specificity of each of the fungal species and the primer sets used.

TABLE 7

Reaction Specificity of Primer Set

|  | Fungal Species | Primer Set Tr | Primer Set Tm |
|---|---|---|---|
| 1 | *Trichophyton rubrum* NBRC 5467 | + | − |
| 2 | *Trichophyton rubrum* NBRC 5807 | + | − |
| 3 | *Trichophyton rubrum* NBRC 9185 | + | − |
| 4 | *Trichophyton mentagrophytes* NBRC 5466 | − | + |
| 5 | *Trichophyton mentagrophytes* NBRC 5809 | − | + |
| 6 | *Trichophyton mentagrophytes* NBRC 5929 | − | + |
| 7 | *Arthroderma vanbreuseghemii* JCM 1891 | − | − |
| 8 | *Arthroderma vanbreuseghemii* JCM 1892 | − | − |
| 9 | *Arthroderma benhamiae* JCM 1885 | − | − |
| 10 | *Arthroderma benhamiae* JCM 1886 | − | − |
| 11 | *Trichophyton tonsurans* NBRC 5928 | − | − |
| 12 | *Malassezia furfur* NBRC 0656 | − | − |
| 13 | *Microsporum canis* NBRC 7863 | − | − |
| 14 | *Candida albicans* NBRC 0197 | − | − |
| 15 | *Aspergillus fumigatus* NBRC 4057 | − | − |
| 16 | *Fusarium solani* NBRC 5232 | − | − |

In the reaction solution containing the primer set Tr, the DNA amplification was detected only when the template DNA contains the gene of *T. rubrum*. In the reaction solution containing the primer set Tm, the DNA amplification was detected only when the template DNA contains the gene of *T. mentagrophytes*. In any of the reaction solutions, the DNA derived from the fungal species other than the *Trichophyton* was not amplified. Therefore, since the genes of *T. rubrum* and *T. mentagrophytes* are specifically amplified by using the reaction solutions containing the primer set Tr and the primer set Tm, respectively, it is found that the presence of a *Trichophyton*, in particular, *T. rubrum* or *T. mentagrophytes* can be specifically detected in samples.

The conventional fungal culture method requires several weeks, for example, eight weeks, to obtain results, has low sensitivity, and requires skilled operations due to a difficulty in culturing specimens derived from tinea unguium, in particular. On the other hand, the LAMP method requires only about two days to obtain results, involves relatively easy operations, and does not need any sophisticated equipment as a matter of course nor even preparation of a selective medium.

As described above, the primer set containing the at least four kinds of oligonucleotides of the present invention makes it possible to specifically detect the *Trichophyton* gene in a sample such as a specimen with high sensitivity by the LAMP method. Then, the detection results are sufficiently comparable to the results obtained by the conventional method, but can be obtained more simply and quickly than those of the conventional method.

It is also possible to detect the *Trichophyton* genes by the LAMP method using primer sets presented in Tables 8 and 9 instead of the primer sets described above in the present specification.

TABLE 8

T. Other Primers Usable for T. rubrum Gene Detection

| Primer | Base Sequence | SEQ ID NO |
|---|---|---|
| 1) Primer Set Tr-II | | |
| TrF3-II | AAGGTTTCCGTAGGTGAACC | 15 |
| TrB3-II | TCGAGGCTCCCAGAAGG | 16 |
| TrFIP-II | GAACGTCGGTCCCTATCGTGGTGCGGAAGGATCATTAACGC | 17 |
| TrBIP-II | GGCCGTACGCCCCCATTCTACGGCTCTCCCTGGCA | 18 |
| TrLF-II | TCTACCTCACCCGGTTGCC | 19 |
| TrLB-II | CAGCCTCCGGCCTGC | 20 |

TABLE 8-continued

T. Other Primers Usable for T. rubrum Gene Detection

| Primer | Base Sequence | SEQ ID NO |
|---|---|---|
| 2) Primer Set Tr-III | | |
| TrF3-III | TGAACCTGCGGAAGGATCA | 21 |
| TrB3-III | TCTTGGTGTCTGTCCTCCG | 22 |
| TrFIP-III | AGAATGGGGGCGTACGGCCTGGCCCCCCACGATAG | 23 |
| TrBIP-III | TCTACCTCACCCGGTTGCCTCGTCGAGGCTCCCAGAAGG | 24 |

TABLE 9

Other Primers Usable for T. mentagrophytes Gene Detection

| Primer | Base Sequence | SEQ ID NO |
|---|---|---|
| 1) Primer Set Tm-II | | |
| TmF3-II | CCACGATAGGGCCAAACG | 25 |
| TmB3-II | CTCAGACTGACAGCTCTTCTG | 26 |
| TmFIP-II | GCCGAGGCAACCGAGTAATGTACGTCAGGGGTGAGCAGAT | 27 |
| TmBIP-II | CGTTCGGCGAGCCTCTCTTTAATTTTTTTGCGTCTGTCCTCC | 28 |
| 2) Primer Set Tm-III | | |
| TmF3-III | TCAGGGGTGAGCAGATGTG | 29 |
| TmB3-III | GCTCAGACTGACAGCTCTTC | 30 |
| TmFIP-III | AACGGCTCTCCTGGGAGAGCCGTACCGCCCCATTCTTG | 31 |
| TmBIP-III | CGGCGAGCCTCTCTTTAGTGGAATTTTTTTGCGTCTGTCCTCC | 32 |

What is claimed is:

1. A primer set for detecting a *Trichophyton* gene by a LAMP method, comprising four primers represented by base sequences of SEQ ID NOs: 1 to 4.

2. The primer set according to claim 1, further comprising at least one loop primer.

3. The primer set according to claim 2, wherein the at least one loop primer is represented by base sequence of SEQ ID NO: 5 or 6.

4. The primer set according to claim 1, wherein the *Trichophyton* gene is of *Trichophyton rubrum*.

5. A kit for detecting a *Trichophyton* gene in a sample, comprising the primer set according to claim 1.

6. The kit according to claim 5, wherein the *Trichophyton* gene is of *Trichophyton rubrum*.

7. A method for detecting a *Trichophyton* gene in a sample, the method comprising the steps of:
amplifying a nucleic acid in the *Trichophyton* gene by a LAMP method with the primer set according to claim 1 or the kit according to claim 5; and detecting the amplified nucleic acid.

8. The method according to claim 7, wherein the amplified nucleic acid is detected by turbidity measurement, fluorescence measurement using a fluorescent substance, immunochromatography, nucleic acid hybridization, or electrophoresis.

9. The method according to claim 7, wherein the *Trichophyton* gene is of *Trichophyton rubrum*.

* * * * *

SEQUENCE LISTING

<160> NUMBER OF SEQ ID NOS: 32

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
aggatcatta acgcgcagg                                              19

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2

```
tcttggtgtc tgtcctccg                                              19

<210> SEQ ID NO 3
<211> LENGTH: 38
<212> TYPE: DNA
<213> ORGANISM: Artificial Sequence
<220> FEATURE:
<223> OTHER INFORMATION: Primer

<400> SEQUENCE: 3
agaatggggg cgtacggccg atagggaccg acgttcca                         38

<210> SEQ ID NO 4
<211> LENGTH: 39
<212> TYPE: DNA
<213> ORGANISM: Artificial Sequence
<220> FEATURE:
<223> OTHER INFORMATION: Primer

<400> SEQUENCE: 4
tctacctcac ccggttgcct cgtcgaggct cccagaagg                        39

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
acgtctgctc acccctga                                               18

<210> SEQ ID NO 6
<211> LENGTH: 15
<212> TYPE: DNA
<213> ORGANISM: Artificial Sequence
<220> FEATURE:
<223> OTHER INFORMATION: Primer

<400> SEQUENCE: 6
ccgcgctccc cctgc                                                  15

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
tgcggaagga tcattagcg                                              19

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
ttttgcgtct gtcctccg                                               18

<210> SEQ ID NO 9
<211> LENGTH: 38
<212> TYPE: DNA
```

```
<213> ORGANISM: Artificial Sequence
<220> FEATURE:
<223> OTHER INFORMATION: Primer

<400> SEQUENCE: 9
caagaatggg gcggtacggc cccacgatag ggccaaac                              38

<210> SEQ ID NO 10
<211> LENGTH: 44
<212> TYPE: DNA
<213> ORGANISM: Artificial Sequence
<220> FEATURE:
<223> OTHER INFORMATION: Primer

<400> SEQUENCE: 10
tacattactc ggttgcctcg gcgcgtttag ccactaaaga gagg                       44

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
tctgctcacc cctgacggac                                                  20

<210> SEQ ID NO 12
<211> LENGTH: 17
<212> TYPE: DNA
<213> ORGANISM: Artificial Sequence
<220> FEATURE:
<223> OTHER INFORMATION: Primer

<400> SEQUENCE: 12
tctcccagga gagccgt                                                     17

<210> SEQ ID NO 13
<211> LENGTH: 710
<212> TYPE: DNA
<213> ORGANISM: Trichophyton rubrum
<300> PUBLICATION INFORMATION:
<308> DATABASE ACCESSION NUMBER: GenBank U18352
<309> DATABASE ENTRY DATE: 1995-02-09
<313> RELEVANT RESIDUES IN SEQ ID NO: (1)..(710)

<400> SEQUENCE: 13
aagtaaaagt cgtaacaagg tttccgtagg tgaacctgcg aaggatcat taacgcgcag        60 gccggaggct ggccccccac gatagggacc gacgttccat caggggtgag cagacgtgcg      120
ccggccgtac gccccccattc ttgtctacct cacccggttg cctcggcggg ccgcgctccc     180
cctgccaggg agagccgtcc ggcgggcccc ttctgggagc ctcgagccgg accgcgcccg     240
ccggaggaca gacaccaaga aaaaattctc tgaagagctg tcagtctgag cgtttagcaa      300
gcacaatcag ttaaaactttt caacaacgga tctcttggtt ccggcatcga tgaagaacgc    360
agcgaaatgc gataagtaat gtgaattgca gaattccgtg aatcatcgaa tctttgaacg     420
cacattgcgc cctctggcat tccggggggc atgcctgttc gagcgtcatt tcaacccctc     480
aagcccggct tgtgtgatgg acgaccgtcc ggcccctccc ttcggggggcg ggacgcgccc    540 gaaaagcagt ggccaggccg cgattccggc ttcctaggcg aatgggcagc caattcagcg     600
ccctcaggac cggccgccct ggccccaatc tttatatata tatatatctt ttcaggttga     660
cctcggatca ggtagggata cccgctgaac ttaagcatat caataagcgg                710
```

-continued

<210> SEQ ID NO 14
<211> LENGTH: 671
<212> TYPE: DNA
<213> ORGANISM: Trichophyton mentagrophytes
<300> PUBLICATION INFORMATION:
<308> DATABASE ACCESSION NUMBER: GenBank KC146353
<309> DATABASE ENTRY DATE: 2013-11-13
<313> RELEVANT RESIDUES IN SEQ ID NO: (1)..(671)

<400> SEQUENCE: 14

```
ggtttccgta ggtgaacctg cggaaggatc attagcgcgc aggccggagg ctggcccccc      60
acgatagggc caaacgtccg tcaggggtga gcagatgtgc gccggccgta ccgccccatt     120
cttgtctaca ttactcggtt gcctcggcgg gccgcgctct cccaggagag ccgttcggcg     180
agcctctctt tagtggctaa acgctggacc gcgcccgccg gaggacagac gcaaaaaaat     240
tctttcagaa gagctgtcag tctgagcgtt agcaagcaaa aatcagttaa aactttcaac     300
aacggatctc ttggttccgg catcgatgaa gaacgcagcg aaatgcgata agtaatgtga     360
attgcagaat tccgtgaatc atcgaatctt tgaacgcaca ttgcgccccc tggcattccg     420
gggggcatgc ctgttcgagc gtcatttcag cccctcaagc ccggcttgtg tgatggacga     480
ccgtccggcg ccccgtctt tgggggtgcg ggacgcgccc gaaaagcagt ggccaggccg      540
cgattccggc ttcctaggcg aatgggcaac aaaccagcgc tccaggacc ggccgccctg      600 gcctcaaaat ctgttttata cttatcaggt tgacctcgga tcaggtaggg atacccgctg     660
aacttaagca t                                                         671
```

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15

```
aaggtttccg taggtgaacc                                                  20
```

<210> SEQ ID NO 16
<211> LENGTH: 17
<212> TYPE: DNA
<213> ORGANISM: Artificial Sequence
<220> FEATURE:
<223> OTHER INFORMATION: Primer

<400> SEQUENCE: 16

```
tcgaggctcc cagaagg                                                     17
```

<210> SEQ ID NO 17
<211> LENGTH: 41
<212> TYPE: DNA
<213> ORGANISM: Artificial Sequence
<220> FEATURE:
<223> OTHER INFORMATION: Primer

<400> SEQUENCE: 17

```
gaacgtcggt ccctatcgtg gtgcggaagg atcattaacg c                          41
```

<210> SEQ ID NO 18
<211> LENGTH: 35
<212> TYPE: DNA
<213> ORGANISM: Artificial Sequence
<220> FEATURE:

<223> OTHER INFORMATION: Primer

<400> SEQUENCE: 18
ggccgtacgc ccccattcta cggctctccc tggca         35

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
tctacctcac ccggttgcc         19

<210> SEQ ID NO 20
<211> LENGTH: 15
<212> TYPE: DNA
<213> ORGANISM: Artificial Sequence
<220> FEATURE:
<223> OTHER INFORMATION: Primer

<400> SEQUENCE: 20
cagcctccgg cctgc         15

<210> SEQ ID NO 21
<211> LENGTH: 19
<212> TYPE: DNA
<213> ORGANISM: Artificial Sequence
<220> FEATURE:
<223> OTHER INFORMATION: Priemr

<400> SEQUENCE: 21
tgaacctgcg gaaggatca         19

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
tcttggtgtc tgtcctccg         19

<210> SEQ ID NO 23
<211> LENGTH: 35
<212> TYPE: DNA
<213> ORGANISM: Artificial Sequence
<220> FEATURE:
<223> OTHER INFORMATION: Primer

<400> SEQUENCE: 23
agaatggggg cgtacggcct ggccccccac gatag         35

<210> SEQ ID NO 24
<211> LENGTH: 39
<212> TYPE: DNA
<213> ORGANISM: Artificial Sequence
<220> FEATURE:
<223> OTHER INFORMATION: Primer

<400> SEQUENCE: 24
tctacctcac ccggttgcct cgtcgaggct cccagaagg         39

```
<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
ccacgatagg gccaaacg                                                 18

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
ctcagactga cagctcttct g                                             21

<210> SEQ ID NO 27
<211> LENGTH: 40
<212> TYPE: DNA
<213> ORGANISM: Artificial Sequence
<220> FEATURE:
<223> OTHER INFORMATION: Primer

<400> SEQUENCE: 27
gccgaggcaa ccgagtaatg tacgtcaggg gtgagcagat                         40

<210> SEQ ID NO 28
<211> LENGTH: 42
<212> TYPE: DNA
<213> ORGANISM: Artificial Sequence
<220> FEATURE:
<223> OTHER INFORMATION: Primer

<400> SEQUENCE: 28
cgttcggcga gcctctcttt aattttttg cgtctgtcct cc                       42

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
tcaggggtga gcagatgtg                                                19

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gctcagactg acagctcttc                                               20

<210> SEQ ID NO 31
<211> LENGTH: 38
<212> TYPE: DNA
<213> ORGANISM: Artificial Sequence
<220> FEATURE:
<223> OTHER INFORMATION: Primer
```

```
<400> SEQUENCE: 31
aacggctctc ctgggagagc cgtaccgccc cattcttg                    38

<210> SEQ ID NO 32
<211> LENGTH: 43
<212> TYPE: DNA
<213> ORGANISM: Artificial Sequence
<220> FEATURE:
<223> OTHER INFORMATION: Primer

<400> SEQUENCE: 32
cggcgagcct ctctttagtg gaatttttt gcgtctgtcc tcc               43
```